United States Patent
Buus et al.

(10) Patent No.: US 9,249,343 B2
(45) Date of Patent: *Feb. 2, 2016

(54) PERMEABLE PRESSURE SENSITIVE ADHESIVE

(71) Applicant: Coloplast A/S, Humlebaek (DK)

(72) Inventors: Hasse Buus, Humlebaek (DK); Mads Lykke, Broenshoej (DK); Tom Kongebo, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 136 days.

This patent is subject to a terminal disclaimer.

(21) Appl. No.: 14/093,757

(22) Filed: Dec. 2, 2013

(65) Prior Publication Data

US 2014/0087183 A1    Mar. 27, 2014

Related U.S. Application Data

(63) Continuation of application No. 13/140,192, filed as application No. PCT/DK2009/050343 on Dec. 18, 2009, now Pat. No. 8,624,078.

(30) Foreign Application Priority Data

Dec. 18, 2008    (DK) .................................. 2008 01811

(51) Int. Cl.
*A61F 13/00*    (2006.01)
*C09J 123/20*    (2006.01)
*C09J 123/08*    (2006.01)
(Continued)

(52) U.S. Cl.
CPC ............. *C09J 123/20* (2013.01); *A61L 15/585* (2013.01); *A61L 24/043* (2013.01); *C09J 7/021* (2013.01); *C09J 123/0853* (2013.01); *C09J 123/22* (2013.01); *A61L 2400/14* (2013.01); *C08K 5/0008* (2013.01); *C08L 23/0853* (2013.01); *C08L 23/22* (2013.01); *C08L 71/02* (2013.01); *C09J 2205/114* (2013.01); *C09J 2423/04* (2013.01); *C09J 2423/10* (2013.01); *C09J 2431/00* (2013.01); *Y10T 428/2848* (2015.01);
(Continued)

(58) Field of Classification Search
CPC ............. C09J 123/0853; C09J 2431/00; C09J 123/0869; C09J 2423/00; C09J 2205/114; C09J 7/021; C09J 123/22; C09J 2423/04; C09J 123/20; C09J 2423/10; A61L 15/585; A61L 24/043; A61L 15/58
USPC ...................................... 602/41–54
See application file for complete search history.

(56) References Cited

U.S. PATENT DOCUMENTS 3,644,252 A    2/1972    Shenfeld et al.
4,477,325 A    10/1984    Osburn
(Continued)

FOREIGN PATENT DOCUMENTS

EP    264299    4/1988
FR    2733508    10/1996
(Continued)

*Primary Examiner* — Michael Brown
(74) *Attorney, Agent, or Firm* — Coloplast Corp., Coloplast A/S; Nick Baumann

(57) ABSTRACT

The present invention relates to a pressure sensitive, hot melt processable adhesive composition comprising a polar plasticizing oil, a polar polyethylene copolymer and polyisobutylene and a layered adhesive construction and a medical device comprising the adhesive composition according to the invention.

17 Claims, 1 Drawing Sheet

(51) Int. Cl.
    *C09J 123/22*     (2006.01)
    *C09J 7/02*     (2006.01)
    *A61L 15/58*     (2006.01)
    *A61L 24/04*     (2006.01)
    *C08K 5/00*     (2006.01)
    *C08L 23/08*     (2006.01)
    *C08L 23/22*     (2006.01)
    *C08L 71/02*     (2006.01)

(52) U.S. Cl.
    CPC ...... *Y10T 428/2878* (2015.01); *Y10T 428/2883* (2015.01)

(56) References Cited

U.S. PATENT DOCUMENTS

| | | | |
|---|---|---|---|
| 4,855,335 A | 8/1989 | Neperud | |
| 5,054,488 A | 10/1991 | Muz | |
| 5,133,821 A | 7/1992 | Jensen | |
| 5,257,491 A * | 11/1993 | Rouyer et al. | 53/428 |
| 5,458,124 A | 10/1995 | Stanko et al. | |
| 6,084,010 A * | 7/2000 | Baetzold et al. | 523/210 |
| 6,372,951 B1 | 4/2002 | Ter-Ovanesyan et al. | |
| 6,385,473 B1 | 5/2002 | Haines et al. | |
| 6,437,038 B1 | 8/2002 | Chen | |
| 6,451,883 B1 | 9/2002 | Chen et al. | |
| 6,559,351 B1 * | 5/2003 | Eakin | 602/56 |
| 2003/0009097 A1 | 1/2003 | Sheraton et al. | |
| 2006/0264549 A1* | 11/2006 | Rolland | 524/425 |
| 2007/0254131 A1* | 11/2007 | Shail et al. | 428/95 |

FOREIGN PATENT DOCUMENTS

| | | |
|---|---|---|
| WO | WO 99/59465 | 11/1999 |
| WO | WO 02/066087 | 8/2002 |
| WO | WO 03/065926 | 8/2003 |
| WO | WO 2009/006901 | 1/2009 |

* cited by examiner

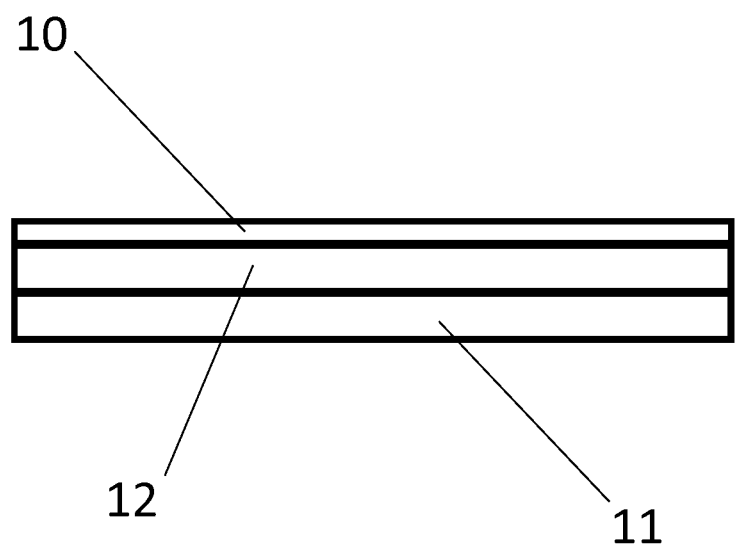

PERMEABLE PRESSURE SENSITIVE ADHESIVE

This is a continuation of Ser. No. 13/140,192, filed, Jun. 16, 2011, which is a 371 of PCT/DK09/50343, filed Dec. 18, 2009, and which has priority of DK PA 200801811 filed Dec. 18, 2008, the disclosures of which are incorporated herein by reference.

FIELD OF THE INVENTION

The present invention relates to a pressure sensitive, hot melt processable adhesive composition comprising polar plasticising oil, a polar polyethylene copolymer and polyisobutylene and a medical device comprising the adhesive composition according to the invention.

BACKGROUND OF THE INVENTION

Pressure sensitive adhesives have for a long time been used for attaching medical devices, such as ostomy appliances, dressings (including wound dressings), wound drainage bandages, devices for collecting urine, orthoses and prostheses to the skin.

Hydrocolloid adhesives containing hydrophilic particles or absorbents, which absorb moisture into the adhesive bulk and transmit moisture when conditions are saturated, are one well-known group of pressure sensitive adhesives useful for attaching medical devices to the skin. However, the retention of moisture in hydrocolloid adhesives may cause changes in the adhesive, such as swelling, loss of cohesion and disintegration. Non-absorbing adhesives on the other hand, may trap excessive moisture between the skin and adhesive, causing weakening of adhesion and maceration of the skin.

An alternative to the absorbing adhesives described above is a liquid impermeable, moisture permeable adhesive such as polyurethane, silicone and polyacrylate.

A liquid impermeable, moisture permeable adhesive does not absorb the moisture but rather permeates the water away from the skin surface. Thus, the swelling effect caused by the hydrocolloids will usually not occur.

U.S. Pat. No. 4,477,325 describes a skin barrier composition made of EVA, PIB and water absorbing particles or polymers. The EVA may contain from 25 to 65% by weight of vinyl acetate.

International Patent Application No. WO 2009/006901 describes pressure sensitive adhesives based on polar ethylene copolymers and a polar oil or a combination of polar oils with an excellent skin adhesion. These adhesives are very soft and have a very high moisture vapour transmission rate, which makes them breathable and very skin friendly.

Optimal adhesives for an ostomy base plate have to perform under a variety of conditions, such as differences in fluidity and amount of stoma exudates, body shape, skin firmness, skin irregularities, activity and perspiration level and of course the variation in the end-users preferred changing pattern of the device. In order to oblige to all these demands, it can sometimes be favourable and easy to add a tackifying component in order to increase the adhesive performance of the adhesive.

Resins are most often added to control the tack, i.e. reduce moduli and increase the glass transition temperature of the adhesive. Resins, however, increase the aggressiveness of the adhesives; this causes stripping of the skin upon removal and consequently makes the adhesives less skin friendly. These adhesives are therefore less suited for end-users who desire a frequent changing pattern but still are reliant on increased adhesive strength.

It has surprisingly been found that using polyisobutylene, even though apolar in nature and with a low glass transition temperature can be added to the polar adhesives described in International Patent Application No. WO 2009/006901 increasing the tack and the adhesive performance and still maintain the necessary storage stability and skin friendliness.

The use of polyisobutylene as a tackifying agent lowers the amount of cell stripping compared to utilizing resins. The addition of an apolar component will cause a decrease in the permeability of the adhesive. However, it has been found that adhesives with a sufficient moist vapour transmission rate to maintain a healthy skin of the end-user can be produced.

SUMMARY OF THE INVENTION

Polymers that may be used in the practice of the invention will generally be copolymers of ethylene and a polar monomer. The copolymers typically comprise less than about 70% ethylene, have water vapour transmission of more than 50 $g/m^2/day$ and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred are ethylene and vinyl acetate copolymers with more than about 40% (w/w) vinyl acetate, a melt flow index of less than 2 g/10 min (190° C./21.1N) and a water vapour transmission of more than 50 $g/m^2/day$ for a 150 μm sheet when measured according to MVTR Test Method.

Polar oils, which may be used in the invention, will generally be those that have good solubility in the polar domains of the polymer, i.e. provide softness without sacrificing too much tensile strength of the polymer. Oils that can support good water vapour permeability are preferred. Examples of such oils are vegetable and animal oils and derivatives thereof. Preferred polar oils are esters, ethers and glycols and particularly preferred is Poly Propylene Oxide, e.g. alpha-butoxy-polyoxypropylene.

Polyisobutylene, with a medium or low molecular weight, are used to increase the tack and the peel properties, while maintaining the skin friendly nature of the adhesive.

It has surprisingly been found that it is possible to obtain stable properties, when mixing polyisobutylene that is apolar and has a low glass transition temperature with the otherwise polar ethylene copolymers and oils.

Additionally, by introducing tacky apolar domains in the otherwise polar adhesive it is to a larger extent possible to customise the adhesive performance by adjusting the properties of either phase.

BRIEF DESCRIPTION OF THE DRAWING

FIG. 1 shows in cross-section a layered adhesive construction comprising a backing layer (10), a first layer of a pressure sensitive adhesive composition (11), and a second layer of a water absorbing adhesive (12).

DETAILED DESCRIPTION OF THE INVENTION

The adhesives of the invention exhibit unique features that make them useful for a variety of applications. Features such as good adhesion to skin, high water vapour transmission rate and skin friendliness are obtained using polar ethylene copolymers, with a suitable polar oil and polyisobutylene and optionally other ingredients.

Adhesives of the invention may be formulated as traditional hydrocolloid containing adhesives providing improved moisture handling properties.

The high moisture vapour transmission rate of the adhesives of the invention makes them very suitable for laminated device constructions with more than one adhesive layer. In example devices, where a non-absorbing substrate contact layer is combined with an absorbing bulk adhesive layer combining tack and durability with good absorption.

In one embodiment of the present invention, a pressure sensitive, hot melt processable adhesive composition comprises a polar plasticising oil or a combination of polar plasticising oils in the content of above 10% (w/w) of the final adhesive and at least one polar polyethylene copolymer and polyisobutylene, wherein the content of the polyethylene copolymer is 5-50% (w/w) of the final adhesive, the polyethylene copolymer has a melt flow index below 2 g/10 min (190° C./21.1N).

In one embodiment of the present invention, a pressure sensitive, hot melt processable adhesive composition is produced by mixing a polar plasticising oil or a combination of polar plasticising oils in the content of above 10% (w/w) of the final adhesive and at least one polar polyethylene copolymer and polyisobutylene, wherein the content of the polyethylene copolymer is 5-50% (w/w) of the final adhesive, the polyethylene copolymer has a melt flow index below 2 g/10 min (190° C./21.1N).

In an embodiment of the invention, the final adhesive in continuous form exhibits moisture vapour transmission rate of at least 100 g/m$^2$/day for a 150 adhesive sheet when measured according to MVTR Test Method.

The primary polymers used in the adhesive composition are ethylene copolymers. The copolymer should contain a considerable amount of a polar component to get high water permeability. Preferably, the ethylene parts of the copolymer can form crystalline areas that ensure the cohesive strength of the adhesive.

In one embodiment of the invention, the polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

The polar polyethylene copolymer is preferably ethylene vinyl acetate.

By polar polymers is meant polymers with water transmission above 50 g/m$^2$/day for a 150 μm film when measured according to MVTR Test Method.

One object of this invention is to provide a water permeable adhesive, i.e. an adhesive, which can be hot-melt processed and which at normal use conditions can be removed without leaving significant residues.

In an embodiment of the invention the ethylene vinyl acetate has a content of at least 40% (w/w) vinyl acetate preferably with 40-80% (w/w) vinyl acetate.

The adhesive composition should fulfil the Dahlquist's criterion. Preferably, the modulus should be below 100,000 Pa, and for very soft, skin friendly and comfortable adhesive the modulus (G') could be as low as 1-30 kPa measured by DMA at 32° C. and 1 Hz.

It is of great importance that the adhesive is as soft as possible to ensure a skin friendly material that is comfortable to wear. To get a soft material, the polymer content should be as low as possible. The maximum polymer content of the polar polyethylene copolymer should not exceed 50% (w/w) of the final adhesive.

Preferably, the polar polyethylene copolymers used in the adhesive should have a molecular structure at a level that results in a melt flow index (MFI) below 2 g/10 min (190° C./21.1N). The melt flow index can be measured by the methods given in ISO 1133 and ASTM D1238.

The advantage of using a polymer with high molecular weight and low MFI is that the high molecular weight polymer can ensure a sufficient high cohesive strength to the adhesive.

By the content of the final adhesive is meant the percentage in weight of the ingredient in relation to the total weight of the ingredients used in the adhesive composition.

In an embodiment of the invention, the content of the polar polyethylene copolymer is 10-45% (w/w) of the final adhesive preferably 15-30%.

In another embodiment of the invention, the polar polyethylene copolymer has a molecular weight above 250,000 g/mol.

In one embodiment of the present invention, the adhesive composition comprises a polar plasticising oil or a combination of polar plasticising oils in the content of 20-70% (w/w) of the final adhesive preferably 30-65% (w/w).

The adhesive should preferably contain about or more than 40% plasticising oil to get the optimal softness and skin friendliness.

In one embodiment of the present invention, the adhesive composition comprises a polar plasticising oil, wherein the polar plasticising oil is selected from the group of liquid rosin derivatives, aromatic olefin oligomers, vegetable and animal oils and derivatives, preferable polar oils are esters, ethers and glycols.

Particularly preferred are poly propylene oxides such as alpha-butoxy-polyoxypropylene. Poly propylene oxide oil contributes to a high permeability of the adhesive composition.

In one embodiment of the invention, the adhesive composition comprises polyisobutylene with a medium or low molecular weight, suited to increase the peel and tack properties of the adhesive. Examples of such polyisobutylenes are Oppanol B10 SFN and Oppanol B12 SFN with molecular weights of 40.000 and 60,000 g/mole respectively.

According to an embodiment of the invention, the polyisobutylene has a molecular weight of below 100,000 g μmol, preferably 40,000-60,000 g/mol.

In one embodiment of the invention, the content of polyisobutylene is 1-30% (w/w) of the final adhesive and preferably the content is 5-20% (w/w) in order to maintain a high moisture vapour transmission rate.

When combining thermoplastic materials that are highly permeable and apolar elastomers with low glass transitions temperature, there is a risk of phase separation/migration. However, the adhesive compositions according to the invention containing polyisobutylene possess sufficient stability.

Some of the adhesive compositions according to the invention contain a minor amount of additional polymer besides the main polymer giving cohesion and the polyisobutylene. This or these additional polymers are added to give tack. These additional polymers are optional and not necessary for all purposes.

In one embodiment of the invention, the adhesive composition further comprises a low molecular weight polymer, i.e. MFI>2.

The addition of a low Mw polymer to the adhesive may be an advantage when a lot of moist is present between the adhesive and the skin.

Preferably the total polymer content, including polar polyethylene copolymer and additional polymers (not including oils, polyisobutylene, tackifier resin etc), should not exceed 50% (w/w) of the final adhesive.

Additional components may be added to the composition such as tackifier resin, plasticisers and wax. The additional components can be used to control the properties of polar phase or the polyisobutylene phase of the adhesives. This is possible by selecting the components that are fully or predominantly compatible with either phase.

In one embodiment of the invention, the adhesive composition further comprises a tackifier resin such as natural, modified or synthetic resins preferably polar resins such as rosins, rosin esters, hydrogenated rosins, hydrogenated rosin esters, and derivatives of such polar resins or pure aromatic monomer resins.

In another embodiment of the invention the adhesive composition comprises an apolar resin compatible with the polyisobutylene section of the adhesive such as hydrogenated hydrocarbon resins.

Tackifier resins can be added to control tack in the adhesives, i.e. reduce moduli and increase glass transition temperature.

The content of the tackifier resin is 0 to 40% (w/w) of the final adhesive. Preferably, the adhesive is substantially free of resin. When the adhesive composition contains resin, the content of the tackifier resin is preferably 0, 1-40% (w/w) of the final adhesive and more preferably 10-20% (w/w) of the final adhesive.

In one embodiment of the present invention, the adhesive composition comprises polar plasticising oils and resin in the content of above 50% (w/w) of the final adhesive.

In one embodiment of the invention, the adhesive composition further comprises an additional plasticiser selected from the group of mineral oil, citrate oil, paraffin oil, phatalic acid esters, adepic acid esters (e.g. DOA), and liquid or solid resin.

In another embodiment of the invention, the adhesive composition further comprises a polyethylene wax.

Other ingredients may be added for auxiliary benefits. This could be antioxidants and stabilisers, fillers for rheology modification or active components like vitamin E or ibuprofen.

In another embodiment of the invention, the adhesive composition further comprises other ingredients selected from the group of antioxidants, stabilisers, fillers, pigments, flow modifiers, and active ingredients.

In one preferred embodiment of the invention, the adhesive composition comprises polar active ingredients.

Salts and/or hydrocolloids, as absorbing particles or polymers, may be added to the composition to create an absorbing material.

Salt may be a water-soluble salt and can be inorganic salt or organic salt.

According to one embodiment of the invention, the adhesive composition comprises water soluble inorganic salt from the group of but not limited to NaCl, $CaCl_2$, $K_2SO_4$. $NaHCO_3$, $Na_2CO_3$, KCl, NaBr, NaI, KI, $NH_4Cl$, $AlCl_3$ and mixtures thereof, preferably NaCl.

According to another embodiment of the invention, the adhesive composition comprises water soluble organic salt from the group of but not limited to $CH_3COONa$, $CH_3COOK$, COONa, COOK and mixtures thereof.

The adhesive can be used without particles in devices, which rely on transmission rather than absorption.

As with traditional HC adhesives, most liquid absorbing polymeric particles can be used, including microcolloids. A special advantage with a permeable adhesive is that a surface film will not block absorption completely.

More particularly, the hydrocolloids may be guar gum, locust bean gum (LBG), pectin, alginates, potato starch, gelatine, xanthan, gum karaya: cellulose derivatives (e.g. salts of carboxymethylcellulose such as sodiumcarboxymethylcellulose, methylcellulose, hydroxyethyl cellulose and hydroxypropylmethylcellulose), sodium starch glycolate, polyvinylalcohol and/or polyethylene glycol.

In one embodiment of the invention, the amount of hydrocolloid is below 60% (w/w) of the total composition.

Microcolloid particles are well known in the art e.g. from International Publication No. WO 02/066087, which discloses adhesive compositions comprising microcolloid particles. The microcolloid particles may have a particle size of less than 20 microns.

The invention also relates to medical devices comprising a pressure sensitive adhesive composition as described above.

The medical device comprising an adhesive composition according to the invention may be an ostomy appliance, a dressing, a skin protective bandage, a device for collecting urine, an orthose or a prosthese, e.g. a breast prothesis, a faecal management device, and electronic device such as a measuring instrument or a power source, such as a battery.

The medical device may also be a tape (e.g. an elastic tape or film), or a dressing or a bandage, for securing a medical device, or a part of the medical device to the skin, or for sealing around a medical device attached to the skin.

The medical device may in its simplest construction be an adhesive construction comprising a layer of the pressure sensitive adhesive composition according to the invention and a backing layer.

The backing layer is suitably elastic (has a low modulus), enabling the adhesive construction to conform to the skin movement and provide comfort when using it.

In a preferred embodiment of the invention, the backing material has a structured surface to improve the adhesion between the adhesive and the backing material. Particularly preferred are backing materials where the molted adhesive can penetrate and create mechanical interlocking with for example Non Woven and non-woven film laminates.

The thickness of the backing layer used according to the invention is dependent on the type of backing used. For polymer films, such as polyurethane films, the overall thickness may be between 10 to 100 μm, preferably between 10 to 50 μm, most preferred about 30 μm.

In one embodiment of the invention the backing layer is non-vapour permeable.

In another embodiment of the invention, the backing layer is water vapour permeable and has a moisture vapour transmission rate above 500 $g/m^2/24$ h. In this case the adhesive construction of the invention may provide a good moisture transmission rate and is able to transport a large quantity of moisture through the construction and away from the skin. Both the chemical composition and physical construction of the adhesive layer and the chemical and physical construction of the backing layer affect the water vapour permeability. With regard to the physical construction, the backing layer may be continuous (no holes, perforations, indentations, no added particles or fibres affecting the water vapour permeability) or discontinuous (it has holes, perforations, indentations, added particles or fibres affecting the water vapour permeability).

The moisture vapour transmission rate of the backing layer is suitably above 500 g/m²/24 h, most preferably above 1,000 g/m²/24 h, even more preferred above 3,000 and most preferred above 10,000.

In another embodiment of the invention, a layered adhesive construction comprises a backing layer and at least one layer of a pressure sensitive adhesive composition according to the invention.

The adhesive according to the invention may be foamed into foamed adhesive in a number of ways, either chemically or mechanically.

Chemical blowing agents or other materials added to the adhesive formula itself may generate gas bubbles by a variety of mechanisms. These mechanisms include but are not limited to chemical reaction, physical changes, thermal decomposition or chemical degradation, leaching of a dispersed phase, volatilisation of low boiling materials or by a combination of these methods.

Any of the commercially known chemical blowing agents may be used. The chemical blowing agents are suitably non-toxic, skin friendly and environmentally safe, both before and after decomposition.

The amount of chemical blowing agent to be added to the adhesive mixture may range from about 0.01% up to about 90% by weight, with a practical range including about 1% up to about 20% by weight. The amount of gas to be added may be determined by measuring the amount of gas generated from a candidate mixture and calculating the amount of foaming required for the final product, tempered by experience of the amount of gas lost to atmosphere during the foaming process.

Another method for creating a foamed adhesive of the invention is a method where a mechanical process is used to add a physical blowing agent, similar to whipping the adhesive mass into froth, thus creating a foamed structure. Many processes are possible including processes involving incorporation of air, nitrogen, carbon dioxide, or other gases or low boiling point volatile liquids during the manufacturing process for the adhesive.

According to a further embodiment, the invention relates to a medical device such as a thin adhesive dressing, wherein the thickness of the adhesive layer is between 50 and 250 µm where it is thickest. The adhesive layer may thus have varying thickens or it may have a uniform thickness selected from values between 50 and 250 µm.

A dressing of the invention may in a preferred embodiment comprise an absorbing pad for the uptake of body fluids, especially wound exudates, so as to enable the wound dressing to keep a constant moist environment over the wound site and at the same time avoid maceration of the skin surrounding the wound.

A dressing of the invention is optionally covered in part or fully by one or more release liners, or cover films to be removed before or during application. A protective cover or release liner may for instance be siliconised paper. It does not need to have the same contour as the dressing and a number of dressings may be attached to a larger sheet of protective cover. The release liner may be of any material known to be useful as a release liner for medical devices.

The protective cover is not present during the use of the dressing of the invention and is therefore not an essential part of the invention. Furthermore, the dressing of the invention may comprise one or more "non touch" grip(s) known per se for applying the dressing to the skin without touching the adhesive layer. Such a non-touch grip is not present after application of the dressing. For larger dressings it is suitable to have 2 or 3 or even 4 "non-touch" grips.

Flexibility in the adhesive part of a medical device is often achieved by device design, such as bevelling or patterning in the adhesive.

A dressing or adhesive sheet of the invention may have bevelled edges in order to reduce the risk of "rolling-up" the edge of the dressing reducing the wear-time. A bevelling may be carried out discontinuously or continuously in a manner known per se e.g. as disclosed in EP Patent No. 0 264 299 or U.S. Pat. No. 5,133,821.

In another aspect, the invention relates to a wafer for an ostomy appliance comprising an adhesive construction as described above.

An ostomy appliance of the invention may be in the form of a wafer forming part of a two-piece appliance or in the form of a one-piece appliance comprises a collecting bag for collecting the material emerging from the stoma. A separate collecting bag may be attached to the wafer by any manner known per se, e.g. through mechanical coupling using a coupling ring or through use of adhesive flanges.

A wafer for an ostomy appliance of the invention also typically comprises a water vapour permeable and water impervious reinforcement material and a release liner as discussed above.

An ostomy appliance of the invention may be produced in a manner known per se from materials conventionally used for the preparation of ostomy appliances.

Devices with advantageous properties may be obtained using the permeable adhesives of the invention in laminated constructions.

In one embodiment of the invention the construction further comprises at least one layer of a water absorbing adhesive.

Devices with very good adhesion under extreme conditions, for example high moisture load from heavy sweating, may be obtained by placing a layer, preferably a thin layer, of permeable but non-absorbing adhesive (no hydrophilic fillers) of the invention between a water absorbing adhesive and the skin. In this way, good adhesive power can be maintained even after the adhesive has absorbed a considerable amount of water.

It is a particular advantage to use the absorbing adhesive constructions according to the invention in connection with ostomy appliances, because the adhesive can be made resistant to the aggressive fluids from the stoma, without sacrificing too much water absorption. Hence, it is possible to make devices which shield the skin efficiently from the corrosive stoma fluids and on the same time provide a healthy non occlusive micro environment between the adhesive and the skin.

In a further embodiment, the invention relates to prosthesis of the type to be adhered to the skin of the user, such as a breast prosthesis comprising an adhesive construction according to the invention.

The invention also relates to a urine collecting device comprising an adhesive construction as described above.

Urine collecting devices according to the invention may be in the form of uri-sheaths.

As mentioned above, the medical device may also be a medical tape e.g. for securing a device or a part of a device to the skin.

The medical device according to the invention may also be a measuring instrument or a therapeutic instrument, which is attached to the skin, such as devices useful for measuring ECG (Electro CardioGraphy), EMG (Electro MyoGraphy), EEG (Electro EncephaloGraphy), blood glucose, pulse, blood pressure, pH, and oxygen.

Such measuring instruments are known in the art and they are usually attached to the skin by a pressure sensitive adhesive.

Examples of such devices are described in e.g. International Publication No. WO 03/065926, U.S. Pat. No. 5,054, 488, U.S. Pat. No. 5,458,124, U.S. Pat. No. 6,372, U.S. Pat. No. 6,385. International Publication No. WO 99/59465 and US application No. 2003/0009097. An adhesive construction in accordance with the present invention may replace the adhesive constructions used for attaching these devices to the skin.

In another embodiment of the invention, the adhesive is part of a faecal-collecting device, attaching a bag or another collecting device to the perianal skin.

EXPERIMENTAL

Laboratory Methods

Method 1: Mixing

The adhesives were compounded in a Brabender mixer from Brabender OHG, Duisburg, Germany (contains about 60 grams) or a Herrmann Linden LK II 0.5 from Linden Maschinenfabrik, Marienheiden, Germany (contains about 600 grams). The chamber temperature in the mixer was approximately 120° C. and the adhesive was compounded with 50-60 rpm.

Premixtures were made from each polymer. The polymer was added to the mixer and the mixer was started. When the polymer was melted and had a smooth surface, oil was added slowly in small steps, starting with a few ml, followed by increasing amounts. The following part of oil was not added until the previous part was well mixed into the polymer.

For Levamelt/PPO adhesives, the ratio between Levamelt and PPO in the premixture was typically approximately 1:1.

The adhesive was compounded from the premixtures of polymer and oil. The premixture was added to the mixer together with polyisobutylene, resin and/or high MFI polymer, if such was used in the formulation. The mixer was started, and when the polymer was melted and had a smooth surface, additional oil was added slowly in small steps, starting with a few ml, followed by increasing amounts.

If the formulation included hydrocolloids or salt, these were added to the adhesive and mixed for approximately 15 minutes.

Method 2: Mechanical Degradation of Precrosslinked Levapren

In some cases, it was necessary to perform a mechanical degradation of the precrosslinked EVA, e.g. when Levapren VPKA 8857 was used. The polymer was mixed for about 10 hours in a cold Hermann Linden LK II 0.5 mixer to get mechanical breakdown of the polymer chains. The heating system was not turned on and the mixing speed kept low, approximately 20 rpm, to ensure optimal mechanical work on the polymer. The breakdown of the polymer was followed by visual inspection of a thermoformed film of the treated polymer. The mechanical treatment was continued until only a minor amount of polymer gel-lumps remained.

Method 3: Gamma Irradiation

Approximately 1 kilo of the polymer was placed in a plastic bag. The bag was packed and sent to the gamma irradiation supplier, e.g. BGS Beta-Gamma Service, Wiehl, Germany. The polymer was irradiated with the specified gamma dose, e.g. 30 kGy. The gamma radiation increases the molar weight of the polymer.

When the polymer was returned, it was mixed with oil, to obtain premixtures as described above.

Method 4: Determination of Moisture Vapour Transmission Rate (MVTR)

MVTR was measured in grams per square meter ($g/m^2$) over a 24 hours period using an inverted cup method.

A container or cup being water and water vapour impermeable having an opening was used. 20 ml saline water (0.9% NaCl in demineralised water) was placed in the container and the opening was sealed with the test adhesive film. The container was placed into an electrically heated humidity cabinet and the container or cup was placed upside down, in a way that the water was in contact with the adhesive. The cabinet was maintained at 37° C. and 15% relative humidity (RH). The weight loss of the container was followed as a function of time. The weight loss was due to evaporation of water vapour transmitted through the adhesive film. This difference was used to calculate Moisture vapour transmission rate or MVTR. MVTR was calculated as the weight loss pr time divided by the area of the opening in the cup ($g/m^2/24$ h). The MVTR of a material was a linear function of the thickness of the material. Thus, when reporting MVTR to characterise a material, it was important to inform the thickness of the material. We used 150 μm as a reference. If thinner or thicker samples were measured, the MVTR was reported as corresponding to a 150 μm sample. Thus, a 300 μm sample with a measured MVTR of 10 $g/m^2/24$ h was reported as having MVTR=20 $g/m^2/24$ h for a 150 μm sample because of the linear connection between thickness of sample and MVTR of sample.

Finally, we noted that by using this method, we introduced an error by using a supporting PU film. The fact that the adhesive/film laminate was a system of two resistances in series eliminated the error. When the film and the adhesive were homogeneous, the transmission rate may be expressed as:

$$1/P(\text{measured})=1/P(\text{Film})+1/P(\text{Adhesive})$$

Hence, by knowing the film permeability and thickness of the adhesive, it was possible to calculate the true permeability of the adhesive (P(Adhesive)) using the following expression:

$$P(\text{adhesive})=d(\text{Adhesive})/150 \text{ micron}*1/(1/P(\text{measured})-1/P(\text{Film}))$$

where d(Adhesive) was the actual measured thickness of the adhesive and P(Film) was the MVTR of the film without any adhesive on and P(measured) was the actual measured MVTR.

Method 5: Determination of Peel Failure Mode

The peel failure mode was determined by peeling a suitable sample from skin.

The peel failure mode, i.e. adhesive or cohesive failure of the adhesive, was visually observed. Cohesive failure was unwanted, as adhesives with cohesive failure were likely to leave residues on the substrate when removed.

The test samples were prepared by thermoforming an approximately 200 micron adhesive film between two release liners. Said adhesive film was transfer coated onto an 80 gsm elastic non-woven from BBA Fiberweb (Dreamex, CS9540002, 80 gsm) and heat treated at 100° C. for about 5 minutes to thoroughly bond the adhesive to the NW. 1 cm wide test specimens were cut along the low module axis of the non-woven.

The test specimens were applied to the underside of the forearm and left for about 2 hours before they were peeled. The results were reported as Adhesive or Cohesive peel failure mode.

Method 6: Determination of Skin Friendliness/Aggressiveness of Adhesive

The test samples were prepared by thermoforming in a 100 micron thick adhesive layer between a release line and a 40 micron PUR film. Sample/strips of 25×100 mm were punched out. Subjects wore strips of 4 different adhesive compositions. Each subject wore 5 strips of each adhesive with a 12 hours changing frequency. The skin evaluation was performed immediately after removal of the last strip and 12 hours after the last strip was removed.

Method 7: Peel Force

The test samples were prepared by thermoforming in a 100 micron thick adhesive layer between a release line and a 25 micron PUR film. Sample/strips of 25×100 mm were punched out.

The release liner was removed and the samples were placed on a Teflon plate and exposed to pressure of 2 kg for a short period of time. After 30 minutes the samples were peeled in a 90° angle from the Teflon plate using an instron 5543 with a 20 N load cell.

Method 8: Tack Force

The test samples were prepared by thermoforming an approximately 100 micron adhesive film between two release liners. A sample of 20×65 mm is punched out and the sample is attached to an object glass and the release liner is removed. A round 10 mm in diameter Teflon probe is used to measure the tack properties of the adhesives.

Method 9: DMA and Determination of G' and Tan(δ)

The parameters G' and tan(δ) were measured as follows: The adhesives were pressed into a plate of 1 mm thickness. A round sample of 25 mm in diameter was cut out and placed in a RheaStress RS600 rheometer from Thermo Electron. The geometry applied was parallel plates 25 mm and the deformation was fixed at 1% to ensure that measurements were in the linear regime. The measurements were carried out at 32° C.

Materials

| Name | Chemistry | Supplier |
| --- | --- | --- |
| Levamelt | Copolymers of ethylene and vinyl acetate (VA). | Lanxess, Germany |
| Polyglycol B01/120 (PPO) | Poly(propylene oxide) oil (Mw = 2000) | Clariant, Germany |
| Kristalex 100 | Aromatic pure monomer hydrocarbon resin | Eastman |
| Oppanol B12 SFN | Polyisobutylene, Mw: 60.000 | BASF |
| Bioflex 130 | PU film, 25 micron | Scapa |
| Dreamex CS9540002 | PU/PE NW, 80 gsm | BBA Fiberweb |

Results

Example 1

Adhesives According to the Invention

The table beneath shows examples of adhesive compositions prepared according to the invention.

| Sample number | STR060.71 | STR060.42 | STR068.05 | STR060.43 | STR068.06 |
| --- | --- | --- | --- | --- | --- |
| Levamelt 700, 22 kGy Gamma MFI <2 | 26 | 24 | 23 | 24 | 23 |
| Levamelt 500, 17 KGy gamma MFI <2 | 10 | 8 | 7 | 8 | 7 |
| Levamelt 700 MFI = 4 | 14 | 10 | 8 | 10 | 8 |
| Polyglycol B01/120 | 50 | 42 | 38 | 42 | 38 |
| Oppanol B12 SNF | | | 16 | 24 | |
| Kristalex 100 | | | | 16 | 24 |
| Tack Force (N) | 4.8 | 5.2 | 6.0 | 5.5 | 6.2 |
| Peel force (N), | 2.2 | 3.0 | 3.5 | 2.6 | 3.2 |
| Peel failure mode | Adhesive | Adhesive | Adhesive | Adhesive | Adhesive |
| Skin evaluation; 12 hours | No visual change | No visual change | Pink/reddish skin | No visual change | Highly red skin |
| Transmission, g/m$^2$/day | 942 | 713 | 361 | 653 | 468 |
| Module, G', 1 Hz/0.01 Hz; Pa | 38300/8065 | 34020/5445 | 38850/6012 | 33060/6139 | 30560/5190 |
| Tanδ, 1 Hz/0.01 Hz | 0.55/0.63 | 0.58/0.73 | 0.61/0.88 | 0.58/0.63 | 0.59/0.69 |

An increase in peel and tack properties can be noted without a change in failure mode. Polyisobutylene (low glass transition temperature) increases the flow properties, thereby increasing the adhesive strength of the adhesives. The polar resin increases the glass transition temperature and lowers the module.

Besides the visual observation, the skin evaluation revealed a 'burning sensation' on the skin on removal of the adhesives containing resins. This sensation was also to some extent experienced on STR068.05 due to the high adhesion and stretching of the skin, but was absent in STR060.42. It was concluded that for similar adhesive properties, the removal of the adhesives containing polyisobutylene was more comfortable than the removal of the adhesives containing resins.

It can also be observed that the decrease in MVTR for the addition of polyisobutylene is a little lower than the resin for 16% (w/w) addition and a little higher for 24% (w/w).

Example 2

Stability of Compositions Containing Polyisobutylene

The adhesive composition STR060.42 was stored at 40° C. for a period of 3 month and the peel and MVTR measurement was repeated.

| | STR060.42 | |
|---|---|---|
| | Transmission; g/m²/day | Peel, 5 mm/s, 100 micron (N) |
| Initial | 713 | 3.5 |
| 40° C., 3 month | 704 | 3.7 |

Only a minor change in MVTR and peel is observed. The deviation is considered to be within the experimental error. DMA spectres of the samples was also recorded and showed no difference in rheological properties as a consequence of storing.

Example 3

Processing Stability—Thermoforming

| Pressed at 100° C. | STR060.42 Transmission; g/m²/day |
|---|---|
| Pressing time 10 sec. | 713 |
| Pressing time 160 sec. | 732 |

Only a minor change in MVTR is observed as the time of the pressing is prolonged. The deviation is considered to be within the experimental error.

The invention claimed is:

1. A layered adhesive construction comprising:
a backing layer;
a first layer of a pressure sensitive adhesive composition comprising a polar plasticising oil or a combination of polar plasticising oils in the content of 30-60% (w/w), at least one polar polyethylene copolymer in a content of 10-45% (w/w), and 1-30% (w/w) of polyisobutylene, the at least one polyethylene copolymer having a melt flow index below 2 g/10 min (190° C./21.1N); and
a second layer of a water absorbing adhesive.

2. The layered adhesive construction according to claim 1, wherein the first layer of a pressure sensitive adhesive composition exhibits a moisture vapour transmission rate of at least 100 g/m²/day for a 150 micrometers thick adhesive sheet when measured according to MVTR Test Method.

3. The layered adhesive construction according to claim 1, wherein the polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

4. The layered adhesive construction according to claim 1, wherein the polar polyethylene copolymer is ethylene vinyl acetate.

5. The layered adhesive construction according to claim 4, wherein the ethylene vinyl acetate has a content of 40-80% (w/w) vinyl acetate.

6. The layered adhesive construction according to claim 1, wherein the polar polyethylene copolymer has a molecular weight of above 250,000 g/mol.

7. The layered adhesive construction according to claim 1, wherein the polar plasticising oil is selected from the group of liquid rosin derivatives, aromatic olefin oligomers, vegetable and animal oils and derivatives, preferable polar oils are esters, ethers and glycols and particularly preferred is poly propylene oxide such as alpha-butoxy-polyoxypropylene.

8. The layered adhesive construction according to claim 1, wherein the polyisobutylene has a molecular weight of below 100,000 g/mol.

9. The layered adhesive construction according to claim 1, wherein the first layer of the pressure sensitive adhesive composition further comprises a tackifier resin.

10. The layered adhesive construction according to claim 9, wherein a content of the tackifier resin is 10-20%.

11. The layered adhesive construction according to claim 1, wherein the first layer of the pressure sensitive adhesive composition further comprises an additional plasticiser selected from the group consisting of mineral oil, citrate oil, paraffin oil, phatalic acid esters, adepic acid esters, and liquid or solid resin.

12. The layered adhesive construction according to claim 1, wherein the first layer of the pressure sensitive adhesive composition further comprises a polyethylene wax.

13. The layered adhesive construction according to claim 1, wherein the first layer of the pressure sensitive adhesive composition further comprises at least one of an antioxidant, a stabiliser, a filler, a pigment, a flow modifier, and an active ingredient.

14. A medical device comprising a layered adhesive construction according to claim 1.

15. The medical device according to claim 14, wherein the backing layer is non-vapour permeable.

16. The medical device according to claim 14, wherein the backing layer is water vapour permeable and has a moisture vapour transmission rate above 500 g/m²/24 h.

17. The medical device according to claim 14, wherein the medical device is selected from the group consisting of a dressing, an ostomy appliance, a prosthesis, a urine collecting device, a faecal management device, a measuring instrument, a therapeutic instrument, a medical tape, and a dressing or bandage for sealing around a medical device on the skin.

* * * * *